(12) United States Patent
Neijzen et al.

(10) Patent No.: US 9,500,584 B2
(45) Date of Patent: Nov. 22, 2016

(54) MULTIPLE EXAMINATIONS OF A SAMPLE

(75) Inventors: Jacobus Hermanus Maria Neijzen, Eindhoven (NL); Wendy Uyen Dittmer, Eindhoven (NL); Mikhail Mikhaylovich Ovsyanko, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 14/125,093

(22) PCT Filed: Jun. 25, 2012

(86) PCT No.: PCT/IB2012/053182
§ 371 (c)(1),
(2), (4) Date: Dec. 10, 2013

(87) PCT Pub. No.: WO2013/001431
PCT Pub. Date: Jan. 3, 2013

(65) Prior Publication Data
US 2014/0118745 A1 May 1, 2014

(30) Foreign Application Priority Data
Jun. 30, 2011 (EP) .................... 11172100

(51) Int. Cl.
| | | |
|---|---|---|
| G01N 21/00 | (2006.01) | |
| G01N 21/59 | (2006.01) | |
| G01N 21/03 | (2006.01) | |
| G01N 21/31 | (2006.01) | |
| G01N 21/552 | (2014.01) | |
| G01N 33/543 | (2006.01) | |
| G01N 21/17 | (2006.01) | |

(52) U.S. Cl.
CPC .......... *G01N 21/59* (2013.01); *G01N 21/0303* (2013.01); *G01N 21/31* (2013.01); *G01N 21/552* (2013.01); *G01N 33/54326* (2013.01); *G01N 21/3151* (2013.01); *G01N 2021/0325* (2013.01); *G01N 2021/1738* (2013.01); *G01N 2021/1742* (2013.01); *G01N 2201/024* (2013.01); *G01N 2201/066* (2013.01)

(58) Field of Classification Search
USPC ......... 356/432–448, 336–338, 364–369, 136
See application file for complete search history.

(56) References Cited

U.S. PATENT DOCUMENTS

| | | |
|---|---|---|
| 5,437,840 A | 8/1995 | King |
| 5,815,276 A | 9/1998 | Fry |
| 6,215,549 B1 | 4/2001 | Suzuki et al. |

(Continued)

FOREIGN PATENT DOCUMENTS

| | | |
|---|---|---|
| EP | 0786665 A1 | 7/1997 |
| EP | 2221603 A1 | 8/2010 |

(Continued)

*Primary Examiner* — Tri T Ton (57) ABSTRACT

An apparatus for examination of a sample includes at least one sample chamber in which the sample can be provided, where the sample chamber has a detection surface; at least one light source for emitting a first input light beam which is totally internally reflected at the detection surface of the sample chamber into a first output light beam, and for emitting a second input light beam which is at least partially transmitted through the sample chamber into a second output light beam. The apparatus further includes at least one light detector for detecting the first and the second output light beams. The sample chamber is elongated and traversed in longitudinal direction by light of the second input light beam.

15 Claims, 5 Drawing Sheets

(56) References Cited

U.S. PATENT DOCUMENTS

| | | |
|---|---|---|
| 2005/0007594 A1 | 1/2005 | Kritchman |
| 2005/0007596 A1 | 1/2005 | Wilks |
| 2006/0138447 A1 | 6/2006 | Schoo et al. |
| 2009/0311773 A1 | 12/2009 | Schick et al. |

FOREIGN PATENT DOCUMENTS

| | | |
|---|---|---|
| WO | 2008072156 A2 | 6/2008 |
| WO | 2009019619 | 2/2009 |
| WO | 2009087519 A2 | 7/2009 |
| WO | 2010134005 A1 | 11/2010 |
| WO | 2011030286 A1 | 3/2011 |
| WO | 2011036638 A1 | 3/2011 |

MULTIPLE EXAMINATIONS OF A SAMPLE

CROSS-REFERENCE TO PRIOR APPLICATIONS

This application is the U.S. National Phase application under 35 U.S.C. §371 of International Application No. PCT/IB2012/053182 filed on Jun. 25, 2012, which claims the benefit of EP11172100.7 filed on Jun. 30, 2011. These applications are hereby incorporated by reference herein.

FIELD OF THE INVENTION

The invention relates to a sensor apparatus, a cartridge, and a method for the optical examination of a sample, particularly a biological sample.

BACKGROUND OF THE INVENTION

The WO 2010/134005 A1 discloses a biosensor device in which a biological sample fluid can be investigated by frustrated total internal reflection (FTIR). In combination with a magnetic labeling by superparamagnetic beads, the apparatus provides versatile means for a qualitative or quantitative detection of target components in the sample.

SUMMARY OF THE INVENTION

It is an object of the invention to provide means that allow for an extended range of applications of biosensors.

The sensor apparatus according to the invention serves for the examination of a sample, for example a biological sample fluid like blood or saliva. The apparatus comprises the following components:

a) At least one sample chamber in which the sample to be examined can be provided. The sample chamber is typically an empty cavity or a cavity filled with some substance like a gel that may absorb a sample substance; it may be an open cavity, a closed cavity, or a cavity connected to other cavities by fluid connection channels.

b) At least one light source for emitting a first input light beam that is totally internally reflected at a detection surface of the sample chamber, yielding a "first output light beam". Moreover, said at least one light source is adapted to emit a second input light beam that is (at least partially) transmitted through the sample chamber, yielding a "second output light beam" after leaving the sample chamber. It should be noted that the expression "the sample chamber" used in connection with the first and the second input light beam may refer to one and the same sample chamber or to two different sample chambers. The light source may for example be a laser or a light emitting diode (LED), optionally provided with some optics for shaping and directing the input light beams. Preferably, a separate light source is provided for the generation of each of the two input light beams.

c) At least one light detector for detecting the first and the second output light beam. The detector may comprise any suitable sensor or plurality of sensors by which light of a given spectrum can be detected, for example photodiodes, photo resistors, photocells, a CCD chip, or a photo multiplier tube.

The sensor apparatus typically also comprises an evaluation unit (realized e.g. by dedicated electronic hardware and/or digital data processing hardware with software) for evaluating the measurements of the first and second output light beam.

The sample chamber of the described sensor apparatus is preferably accommodated in a separate, changeable cartridge that is designed according to the requirements of the present invention. Accordingly, the invention also relates to a cartridge for use in a sensor apparatus of the kind described above, said cartridge comprising:

a) At least one sample chamber in which the sample can be provided.

b) First optical elements for directing a first input light beam to a detection surface of the sample chamber under an angle of total internal reflection, and for directing the resulting first output light beam out of the cartridge.

c) Second optical elements for directing a second input lighting beam through the sample chamber and for directing the resulting second output light beam out of the cartridge. The first and the second optical elements may for example be provided by reflecting and/or refracting facets that are oriented in a suitable way with respect to the intended light paths.

According to a further aspect, the invention relates to a method for examining a sample, said method comprising the following steps:

a) Filling at least one sample chamber with the sample to be examined.

b) Directing a first input light beam to a detection surface of the sample chamber such that it is totally internally reflected into an output light beam.

c) Directing a second input light beam through the sample chamber such that it yields a second output light beam.

d) Detecting the first and the second output light beams. The detection results of the first output light beam can particularly be evaluated with respect to frustrated total internal reflection. The detection results of the second output light beam may be evaluated with respect to optical absorption characteristics of the sample, particularly the optical absorbance of atoms, molecules, complexes etc. (with or without e.g. magnetic labels).

As the sensor apparatus, the cartridge, and the method relate to different embodiments of the invention, explanations or definitions that are provided for one of them is analogously valid for the other embodiments, too.

The sensor apparatus, the cartridge, and the method allow for a parallel investigation of a sample by two different optical methods, namely a first method that applies total internal reflection at a detection surface and a second method that applies transmission of light through the sample. Thus it is for instance possible to combine in one and the same apparatus capabilities of immunoassays and clinical chemistry.

In the following, various preferred embodiments of the invention will be described that relate to the apparatus, the cartridge, and the method defined above.

In a first particular embodiment, the first output light beam and the second output light beam are detected with the same light detector. Using one and the same detector for both output light beams has the advantage that hardware costs, space consumption, and maintenance effort are minimized. Even with a single light detector, a distinction between detector signals resulting from the first or the second output light beam can readily be achieved. For example, the first and second input light beams may be switched on and off in an alternating manner, they may be modulated with different characteristic frequencies, or they may have different spectra. Each of these measures allows to distinguish detected output light with respect to its origin from the first or the second input light beam, respectively.

At least one of the light detectors that is used to detect the first and/or the second output light beam may comprise an image sensor. With an image sensor, processes in an extended area can be observed simultaneously. An image sensor may particularly be used in combination with the aforementioned embodiment, i.e. as a single light detector for both the first and the second output light beam. In this case the two output light beams may be mapped onto different regions of the image plane, yielding a spatial separation of the contributions of the first and the second output light beam.

A light detector that comprises an image sensor may particularly be focused onto the surface of the sample chamber through which the second output light beam leaves the sample chamber. This implies that the light detector is capable to detect the second output light beam. Preferably, the image sensor is simultaneously focused onto the detection surface, thus allowing to detect the first output light beam, too.

According to a preferred embodiment of the invention, the first and the second input light beams are substantially parallel to each other outside the cartridge (in the context of the present application, the term "substantially" shall indicate a deviation of less than about 45°). In this case the light sources that generate the input light beams can be arranged close to each other, allowing a compact design of the sensor apparatus that is similar to a design with a single light source only. Optionally the first and the second light beam may also be generated by one and the same light source, the emission of which is split into the two input light beams.

The cartridge may particularly comprise an entrance window through which the first and/or the second input light beam can enter the cartridge and that is tilted with respect to the detection surface. Similarly, the cartridge may optionally comprise an exit window through which the first and/or the second output light beam can leave the cartridge and that is tilted with respect to the detection surface. The tilted entrance (or exit) window provides a simple optical means that allows to illuminate (observe) the cartridge from a convenient direction, for example from below with respect to the detection surface.

According to another preferred embodiment of the invention, light from the second input light beam passes through the sample chamber in a direction that is substantially perpendicular to the direction of the first input light beam. This allows to independently choose the design parameters of the sample chamber in two directions according to the requirements of the first and the second input light beam, respectively.

The sample chamber is preferably elongated and traversed in longitudinal direction by light of the second input light beam. In this way the path length of the second input light beam within the sample chamber is increased, providing a higher sensitivity in absorption measurements. The aspect ratio of the sample chamber (i.e. the ratio between the smallest and the largest diameter of the sample chamber) preferably ranges between about 1:5 and 1:100. An elongated sample chamber may particularly be used in the aforementioned embodiment, in which the first and the second input light beams propagate in perpendicular directions when interacting with the sample.

The above defined second optical elements of the cartridge may particularly comprise reflection elements for changing the direction of the second input light beam. Such a reflection element may for example be realized by prismatic structures integrated into the body of the cartridge. With the help of reflection elements, the direction from which an input light beam enters the cartridge may be chosen independently from the direction in which it propagates inside the cartridge.

In another embodiment of the invention, the second input light beam partially propagates through the cartridge (or, more generally, through the material comprising the sample chamber) via a reference path, which comprises no sample, yielding a third output light beam that leaves the cartridge. The reference path may for example be a transparent channel extending in the body of the cartridge parallel to the sample chamber such that the parts of the second input light beam travel on parallel paths through the cartridge with and without encountering sample, respectively. A comparison of the second and the third output light beams will then allow to distinguish changes which originate from variations of the second input light beam (e.g. fluctuations of the light source) from effects caused by the sample (i.e. the effects one is actually interested in).

Preferably, the second input light beam can be switched between different spectra, for example between two monochromatic emissions. Optical absorption or extinction measurements can then be made using optimal parameters with respect to the target component and/or with a high dynamic range.

A magnetic field generator, for example a permanent magnet or an electromagnet, may optionally be provided for generating a magnetic field inside the sample chamber. With the help of a magnetic field, it is for example possible to manipulate magnetically labeled particles. The magnetic field is preferably constant (e.g. zero) during measurements with the second input light beam.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

In the following, the invention will be described with respect to the particular example of a magnetic label biosensor for rapid, sensitive and easy-to-use molecular diagnostics.

The exemplary biosensor apparatus considered here uses an immunoassay in which biological targets labeled with magnetic particles are detected. The optical principle of frustrated total internal reflection (FTIR) is used to sensitively monitor the presence of magnetic nanoparticles on a binding surface.

Although immunoassays are well suited for the detection of proteins via a label, many standard biological assays detect biomolecules using optical absorption of a generated signal to quantify the presence of a target molecule. Typical targets that are easily measured via visible absorption techniques include electrolytes, metabolites and small molecules. It is therefore desirable to have a biosensor apparatus that offers a broad menu of tests simultaneously with one device.

Figure 1:
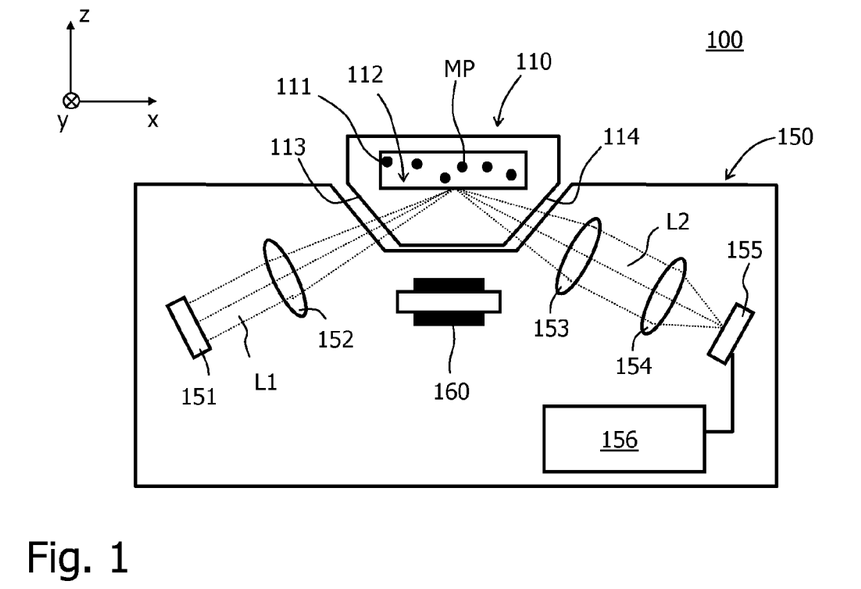
FIG. 1 schematically shows a section along line I-I of FIG. 2 for a sensor apparatus according to a first embodiment of the present invention.
Figure 2:
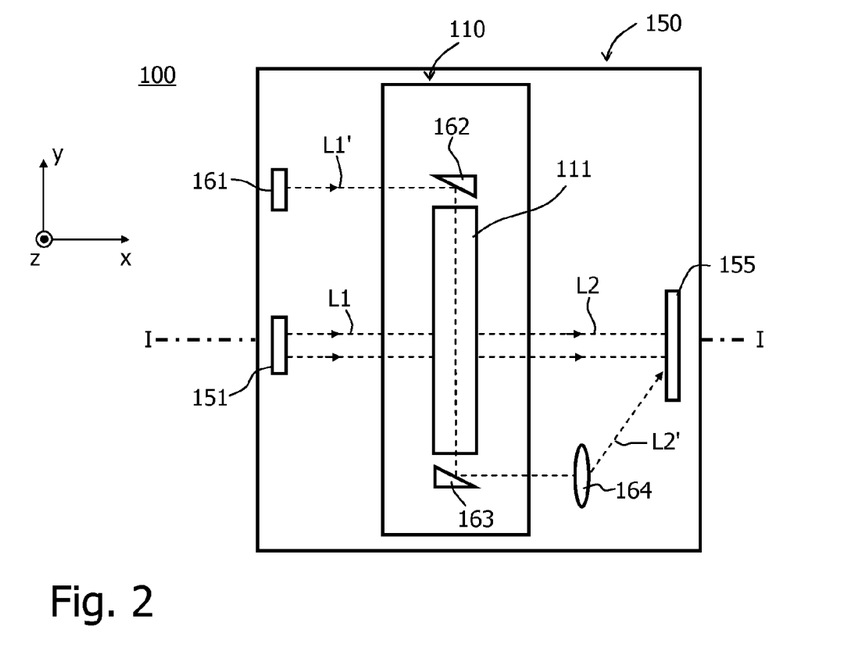
FIG. 2 shows a top view of the sensor apparatus according to FIG. 1.

FIGS. 1 and 2 show a biosensor apparatus 100 that addresses the aforementioned objective, wherein the schematic sectional view of FIG. 1 comprises only components of the FTIR-measurement branch. The sensor apparatus 100 comprises a reader 150 and a disposable cartridge 110 in which a sample with target components of interest can be provided. The cartridge 110 may for example be made from glass or transparent plastic like poly-styrene. It comprises a sample chamber 111 in which a sample fluid with target components to be detected (e.g. drugs, antibodies, DNA, parathyroid hormone PTH etc.) can be provided. The sample further comprises magnetic particles MP, for example superparamagnetic beads, wherein these particles MP are usually bound as labels to the aforementioned target components (for simplicity only the magnetic particles MP are shown in the Figure). It should be noted that instead of magnetic particles other label particles, for example electrically charged or fluorescent particles, could be used as well.

The cartridge 110 has a transparent body with a "detection surface" 112 that (partially) borders the sample chamber 111. A plurality of "detection spots" may be disposed on the detection surface 112. They comprise binding sites, e.g. antibodies, which can specifically bind the target components.

The reader 150 further comprises a magnetic field generator, for example comprising electromagnets 160 with a coil and a core disposed at the bottom and/or at the top (not shown) of the cartridge, for controllably generating a magnetic field at the detection surface 112 and in the adjacent space of the sample chamber 111. With the help of this magnetic field, the magnetic particles MP can be manipulated, i.e. be magnetized and particularly be moved (if magnetic fields with gradients are used). Thus it is for example possible to attract magnetic particles MP to the detection surface 112 in order to accelerate the binding of the associated target component to said surface.

The reader 150 further comprises a magnetic field generator, for example comprising electromagnets 160 with a coil and a core disposed at the bottom and/or at the top (not shown) of the cartridge, for controllably generating a magnetic field at the detection surface 112 and in the adjacent space of the sample chamber 111. With the help of this magnetic field, the magnetic particles MP can be manipulated, i.e. be magnetized and particularly be moved (if magnetic fields with gradients are used). Thus it is for example possible to attract magnetic particles MP to the detection surface 112 in order to accelerate the binding of the associated target component to said surface.

The described sensor apparatus 100 applies optical means for the detection of magnetic particles MP and the target components one is actually interested in. For eliminating or at least minimizing the influence of background (e.g. of the sample fluid, such as saliva, blood, etc.), the detection technique is surface-specific. This is achieved by using the principle of frustrated total internal reflection. This principle is based on the fact that an evanescent wave propagates (exponentially dropping) into the sample chamber 111 when the incident light beam L1 is totally internally reflected. If this evanescent wave then interacts with another medium having a different refractive index from water like the magnetic particles MP, part of the input light will be coupled into the sample fluid (this is called "frustrated total internal reflection"), and the reflected intensity will be reduced (while the reflected intensity will be 100% for a clean interface and no interaction). Further details of this procedure may be found in the WO 2008/072156 A2, which is incorporated into the present text by reference.

An essential feature of the present invention is that the requirements for the above described FTIR detection (immunoassays) and for absorbance detection (clinical chemistry) are combined in one and the same apparatus/cartridge. The objective thereby is to comply to FTIR boundary conditions (cartridge form factor, optical configuration) and absorbance requirements (sufficient path length, reference light path). On top of that one has to deal with finger-prick restrictions leading to minimal plasma sample volumes (about 1 µL at per reaction chamber in a multi-chamber cartridge).

In particular, the FTIR restrictions are:
flat cartridge form factor to keep space for top magnet and bottom magnets;
illumination branch and detection branch under 70° with respect to detection surface;
fixed focus position of the detection branch;
body of cartridge is formed by an injection molded part;
Absorbance restriction are:
long path length;
minimal sample volume due to the finger-prick sample;
reference light path desirable to monitor light source fluctuations;
options to choose the absorption wavelength range desirable.

According to the exemplary embodiment described below, the above requirements are fulfilled with a cartridge with inbuilt optical features and a small volume, long path length chamber that enables optical absorption to be measured using an FTIR reader. The absorbance requirement, i.e. to combine minimal sample volume with a reasonable absorption path length, makes it attractive to create a long and narrow fluidic structure (almost a wave guide) filled with sample. This channel is traversed by the probing light beam.

FIG. 2 shows a schematic top view onto the sensor apparatus 100 of FIG. 1. It can be seen that the sample chamber 111 of the cartridge 110 is actually elongated with an axial extension (y-direction) perpendicular to the direction of the first input light beam L1 (x-direction). The cartridge consists of an injection molded base part containing the reaction chambers and the fluidic channels for supply and exhaust. The fluidic structures are closed on the top side by an adhesive foil. The fluidic supply and exhaust channels to the sample chamber are not drawn in FIG. 2. Typical dimensions for the height and depth of the chamber 111 are 200-400 μm and 5-10 mm for the chamber length, leading to a sample volume of about 0.5-1 μL. A kind of waveguide is created for the light traversing the chamber 111. Although the refractive index of the sample is typically lower than the refractive index of the cartridge, which means that it is not a total internal reflection (TIR) waveguide, the reflections on the chamber sidewalls are still considerable for a well collimated incoming light beam.

The long narrow extension of the sample chamber 111 is used for absorption measurements. To this end, a second light source 161 is provided that emits a second input light beam L1' into the cartridge 110. Within the cartridge, said second input light beam L1' is totally internally reflected by a prism 162 such that it next passes through the sample chamber 111 in axial direction. The light of the second input light beam L1' leaves the sample chamber 111 through an exit facet/surface as a second output light beam L2'. This second output light beam L2' is redirected by a second TIR prism 163 into a direction that is parallel to the direction of the first output light beam L2. With the imaging optical elements 153, 154 and/or an optional additional element 164, the second output light beam L2' is directed onto the image sensor 155. The sensor signal that arises from the second output light beam L2' can then be evaluated by the evaluation unit 156 with respect to the optical absorbance of certain target components of the sample. It should be noted that these evaluated measurements of the second output light beam L2' were preferably obtained when a given, constant magnetic field (particularly a vanishing field) was present in the sample.

In the described cartridge 110, the two prisms 162, 163 are TIR structures, created by indentations in the injection molded cartridge. The orientation of the reflecting surface of these structures is such that the standard 70° angle of incidence is maintained for the second input light beam L1' and the second output light beam L2' with respect to the normal of the detection surface 112. Another advantage of this configuration is that the focus position of the detection branch coincides with the exit facet of the "sample waveguide" 111.

The described apparatus 100 (consisting of the reader 150 and the disposable cartridge 110) allows with one measurement the sensitive detection of magnetic particles on a detection surface and the sensitive detection of extinction (optical absorption) in the bulk volume of a fluid. This combination of detections permits a user to run a variety of different tests using one device. With a disposable cartridge containing several chambers, each for a different molecule to be tested, it is also possible for the user to obtain with one sample and one run results for multiple molecules ranging from proteins to electrolytes. The disposable cartridge can be designed to use a small sample volume which allows for finger-prick blood to be used, a great convenience for the person to be tested.

FIGS. 3-6 illustrate how different angles of incidence for the illuminating second input light beam can be combined with a standard detection angle. The detection branch stays unchanged in all shown embodiments, while the illumination branch offers the flexibility to increase the absorbance path length or to use other light sources than the standard FTIR read-out LED.

Figure 3:
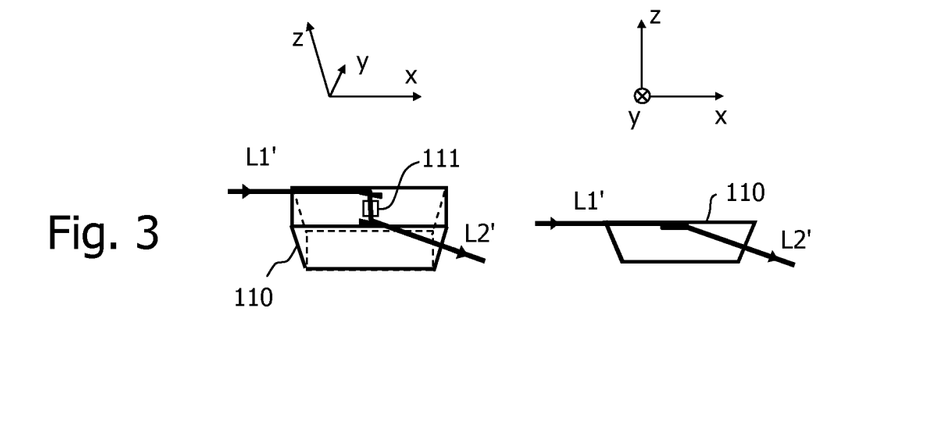
FIG. 3 illustrates the path of the second input light beam in a schematic perspective view (left) and a side view (right) of the sensor apparatus according to FIG. 1.

In FIG. 3, the design of the cartridge 110 is once more illustrated in a schematic perspective view (left) and a side view (right). It can be seen that the second output light beam L1' enters the cartridge 110 from a lateral position (90° with respect to normal of detection surface). The orientation of one of the TIR structures in the injection molded cartridge base part has to be adapted accordingly.

Figure 4:
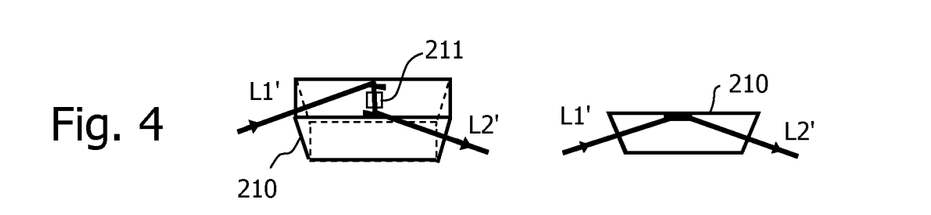
FIG. 4-6 show, in a representation similar to FIG. 3, other possible paths of the second input light beam.

In the cartridge 210 of FIG. 4, the "standard" 70° angles of incidence (second input light beam L1') and detection (second output light beam L2') are realized.

Figure 5:
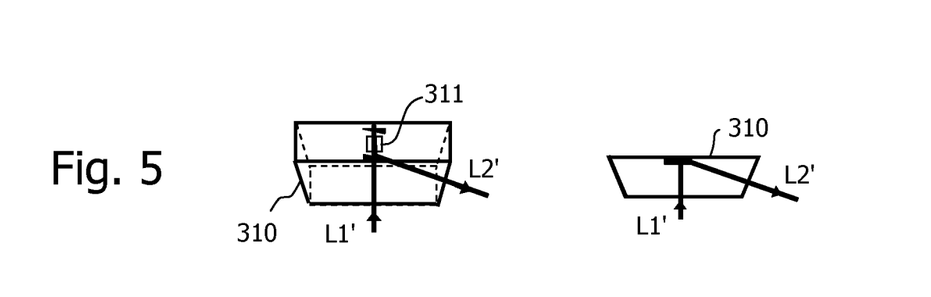

In FIG. 5, the second input light beam L1' enters the cartridge 310 from below (0°).

Figure 6:
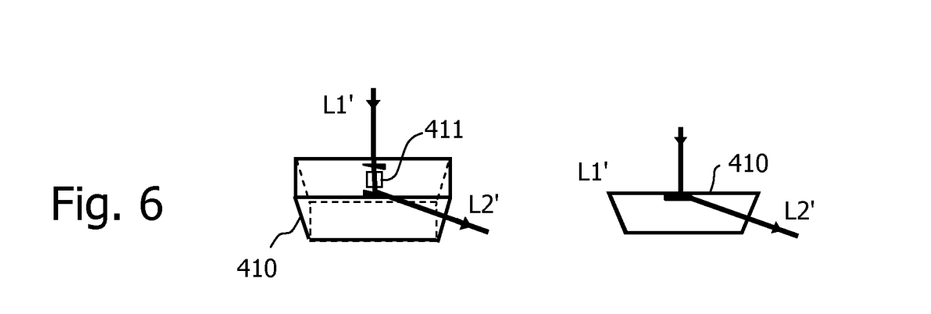

In FIG. 6, the second input light beam L1' enters the cartridge 410 from above (180°).

Figure 7:
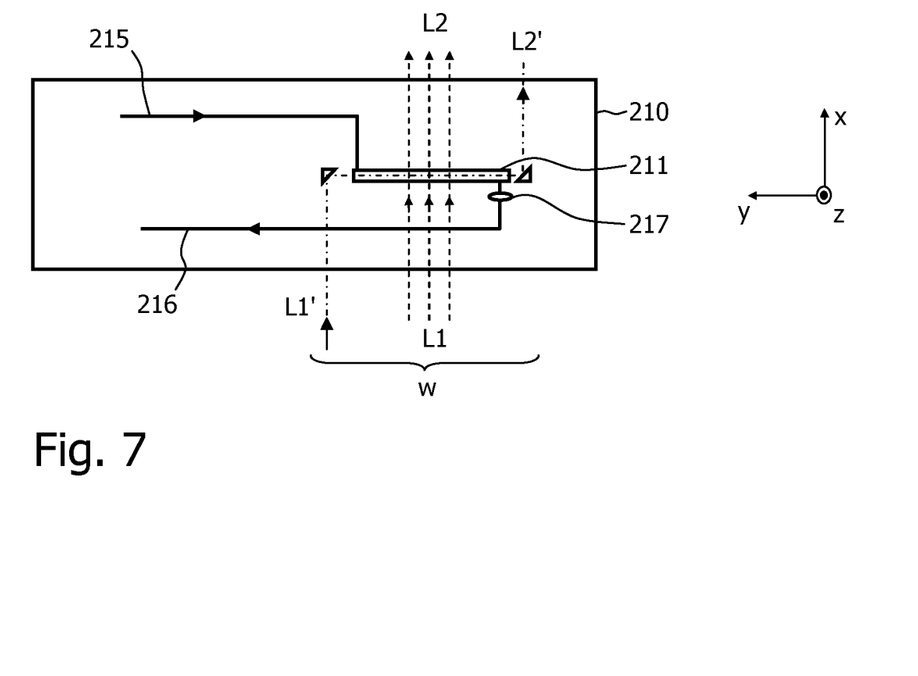
FIG. 7 is a top view of the cartridge of FIG. 4, showing that the second input light beam enters through the entrance window.

FIG. 7 shows a schematic top view of the cartridge 210 of FIG. 4. The fluidic channel 215 for supply of plasma to the sample chamber 211 and the channel 216 for venting are also shown. The elliptical structure 217 in the venting channel represents a fluidic stop. It can be seen that the illumination beams L1, L1' and the detection beams L2, L2' are positioned within the area W of the tilted entrance and exit windows of the cartridge 210. This means that the standard illumination and detection branches of the FTIR platform can be used. A drawback of this configuration is the limited optical path length of the absorbance chamber 211.

A typical width of the field of view of the image sensor 155 is of the order of 6 mm. The length of the tilted (70°) entrance window 113 and exit window 114 in the cartridge 110 for the illuminating and imaging beams is about 9 mm. This limits the maximum absorption path length when the standard FTIR optical configuration is used. If a dedicated (and shifted) second input light beam is used the length of the light path can be increased, while the end facet of the sample chamber stays within the field of view of the camera 155. An additional advantage of a dedicated illumination beam for absorbance with a separate light source is that one is free to choose the optimal wavelength range (LED). A consequence of a shift of the illuminating beam is that the tilted cartridge side window is no longer available.

Figure 8:
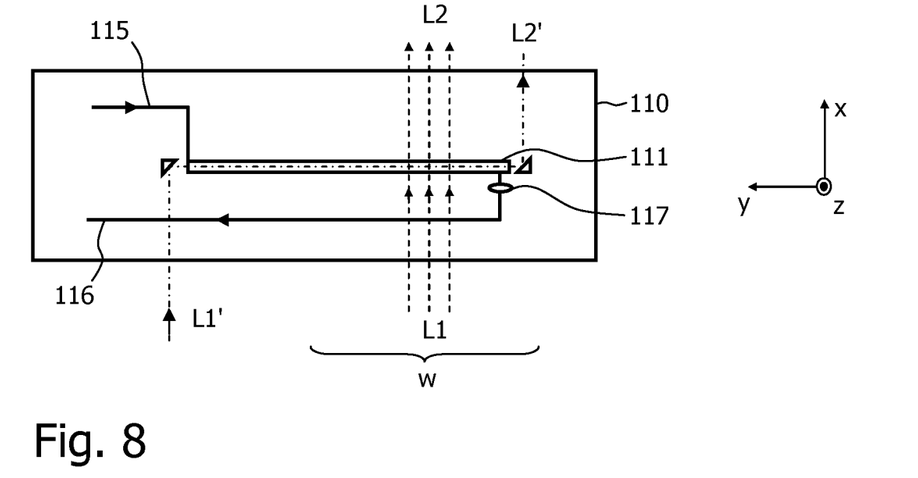
FIG. 8 is a top view of the cartridge of FIG. 1, in which the second input light beam enters outside the entrance window.

FIG. 8 is a more detailed schematic top view of the cartridge 110 of FIGS. 1-3. Here, the second input light beam L1' is not positioned within the area W of the tilted side windows 113, 114 of the cartridge 110. This means that a dedicated illumination beam L1' for the absorbance measurement has been added. According to FIG. 6, this second input light beam L1' enters the cartridge 110 from a 90° lateral position. FIGS. 4-6 show other options regarding the orientation of the illuminating beam. The orientation of the in-coupling prism 162 has to be adopted accordingly.

Figure 9:
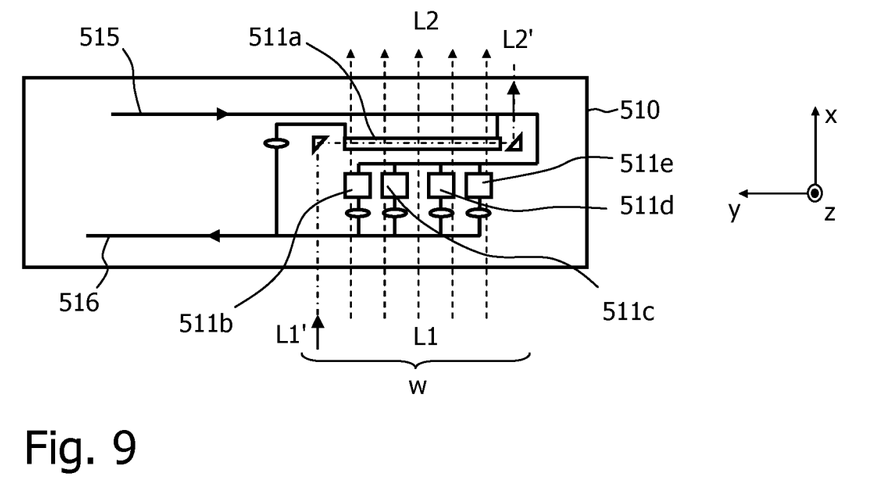
FIG. 9 is a top view of an alternative cartridge in which one elongated sample chamber for absorption measurements is arranged parallel to several separate sample chambers for FTIR measurements.
Figure 10:
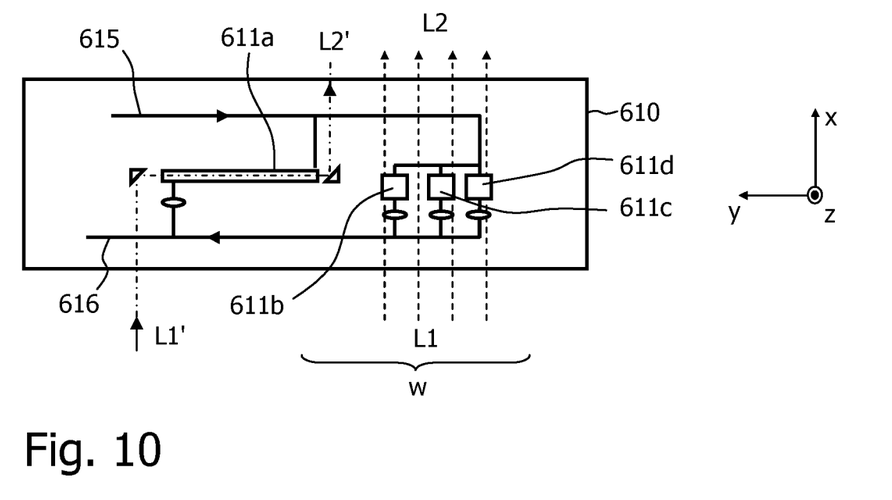
FIG. 10 is a top view of an alternative cartridge in which one elongated sample chamber for absorption measurements is arranged in line with several separate sample chambers for FTIR measurements.

FIGS. 9 and 10 indicate a possibility to combine the absorbance detection chamber with a number of standard immuno-assay reaction chambers. The fluidic channels for supply of plasma and for venting are also shown. The elliptical structures in the venting channels represent fluidic stops. FIG. 9 shows a cartridge 510 in which all input light beams and output light beams are situated within the area W covered by the slanted cartridge side windows (the illumination and detection beams for the immuno-assay chambers are not indicated). The elongated absorbance detection sample chamber 511a and the standard immuno-assay reaction chambers 511b-511e are disposed parallel to each other. The position of the absorbance detection chamber 511a and the prism in the detection light path is chosen such that the exit facet of the detection chamber 511a is in the focal plane of the detection branch. In this way the exit facet is sharply imaged on the detection camera.

FIG. 10 shows a schematic top view of a cartridge 610 comprising an elongated absorbance detection chamber 611a that is arranged in line with three FTIR chambers 511b-511d. The second input light beam L1' for the absorbance measurement is not positioned within the area W of the tilted side windows of the cartridge, enabling a longer light path and a dedicated light source.

Figure 11:
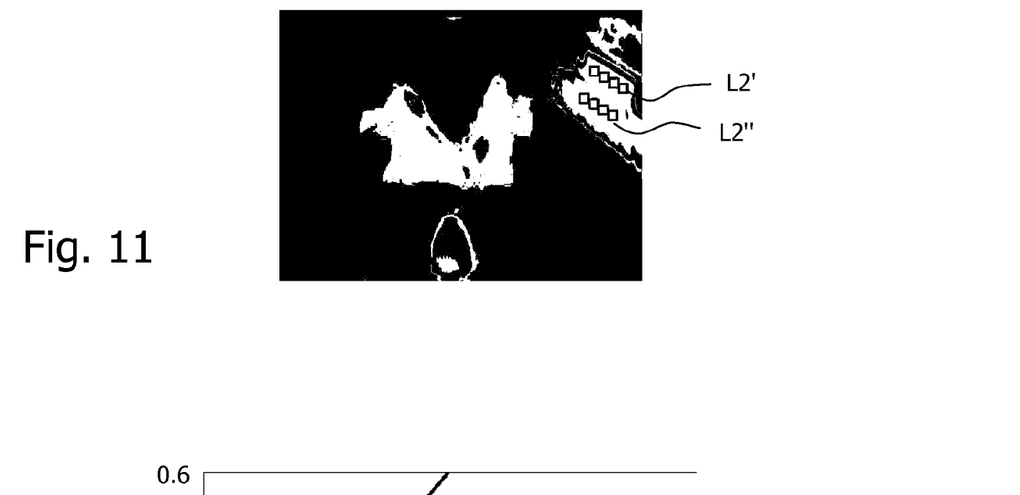
FIG. 11 shows an exemplary camera image of a cartridge.

FIG. 11 shows an exemplary camera image as it can be generated with the apparatus and cartridge embodiments described above. The camera image shows the end facet of the absorbance channel near the edge of the camera's field of view (indicated by L2'; the squares indicate regions of interest in which the image is evaluated). Next to that an area indicated as L2" can be seen where the light has not passed the fluid but only substrate material of the cartridge. Within this area, a third output light beam L2" is detected which originates from a part of the second input light beam L1' that has only traversed the cartridge material and not the sample fluid. This area can hence be used for reference measurements in order to monitor light source fluctuations.

The performance of the described apparatus and the measurement principle has been tested using a series of diluted ink samples. The main objective was to examine the linearity of the low concentration range and the limit of detection and to compare the results to UVVIS results on the same samples.

Figure 12:
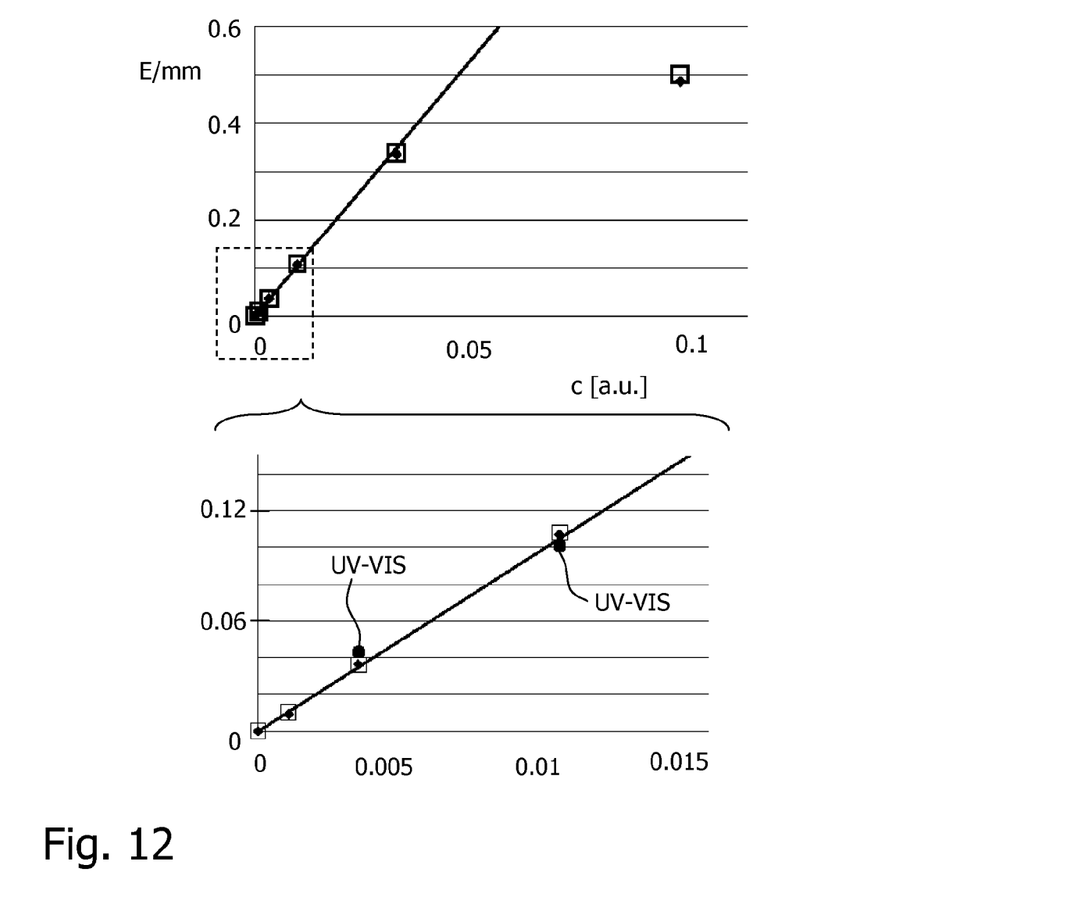
FIG. 12 comprises a diagram (top) representing absorbance measurements made with an apparatus according to the invention, and a detail (bottom) of this diagram.

The top diagram of FIG. 12 shows the Dose-Response curves obtained in the measurements, wherein the low concentration range (dotted square) is shown enlarged in the lower diagram. The absorbance/mm (E/mm) is plotted along the vertical axis, because the path length of the UVVIS (10 mm) differs from the used cartridge path length (3.9 mm). The horizontal axis represents the concentration c (arbitrary units). The low concentration range shows a nicely linear relation between ink concentration and absorbance. Also the agreement with the UVVIS results is very satisfactory. A UVVIS wavelength close to the central wavelength of the reader's light source (LED with $\lambda=635$ nm) was used for this comparison. At high ink concentrations the curve deviates from linear (top diagram), yielding an increased dynamic range. The limit of detection estimated from these preliminary measurements is comparable or better than specified for the UVVIS.

It should be noted that the choice of the optical path length of the absorption chamber depends on the sample properties and the desired measurement range. For optimum sensitivity the natural choice is to use a strongly absorbing wavelength (LED) and a maximum path length. The dynamic range can easily be extended by use of an additional second read-out wavelength (LED) for which the absorbance is substantially lower. It requires that the reader can provide a probing light beam that can switch between several different spectra. This can easily be realized with several LEDs behind an intermediate diffuser or with dichroic mirrors. The capability to switch between different light sources is useful anyhow, since different assays may have different optimal probing wavelengths.

In summary, cartridge embodiments have been described that allow an optical extinction measurement on an FTIR platform using a small sample volume. This enables a measurement system (analyzer+disposable cartridge) that combines immuno-assay capability (based on FTIR detection) with a clinical chemistry measurement (based on absorbance detection). The two measurement techniques can be combined in one integrated cartridge. This is realized by a proper choice of the geometry of the absorbance detection chamber and by adding optical features in the cartridge to redirect the light path, e.g. by means of total internal reflection.

The invention can be used in disposable bio sensor cartridges for handheld diagnostics as well as in the field of clinical chemistry.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A sensor apparatus for the examination of a sample, comprising:
    at least one sample chamber in which the sample can be provided, said sample chamber comprising a detection surface;
    at least one light source for emitting a first input light beam, which is totally internally reflected at the detection surface of the sample chamber into a first output light beam, and for emitting a second input light beam, which is at least partially transmitted through the sample chamber into a second output light beam; and
    at least one light detector for detecting the first and the second output light beams,
    wherein the sample chamber is elongated and traversed in longitudinal direction by light of the second input light beam.

2. The apparatus according to claim 1, wherein the sample chamber is comprised in a cartridge, said cartridge further comprising:
    first optical elements for directing a first input light beam to a detection surface of the sample chamber under an angle of total internal reflection and for directing the resulting first output light beam out of the cartridge;
    second optical elements for directing a second input light beam at least partially through the sample chamber and for directing the resulting second output light beam out of the cartridge.

3. A method for examining a sample, comprising the following acts of:
    filling at least one sample chamber with the sample, said sample chamber being elongated and comprising a detection surface;
    directing by first optical elements a first input light beam to the detection surface of the sample chamber such that it is totally internally reflected into a first output light beam;
    directing by second optical elements a second input light beam at least partially through the sample chamber such that it traverses the sample chamber in a longitudinal direction, yielding a second output light beam;
    detecting the first and the second output light beams by at least one light detector.

4. The apparatus according to claim 1,
    wherein the first output light beam and the second output light beam are detected with the same light detector.

5. The apparatus according to claim 1,
wherein the first output light beam and/or the second output light beam are detected with a light detector that comprises an image sensor.

6. The apparatus according to claim 5,
wherein said light detector is focused onto the surface of the sample chamber through which the second output light beam leaves the sample chamber.

7. The apparatus according to claim 2,
wherein the first and the second input light beams are substantially parallel to each other outside the cartridge.

8. The apparatus according to claim 2,
wherein the first optical elements comprise an entrance window through which the first input light beam and/or the second input light beam can enter the cartridge and that is tilted with respect to the detection surface.

9. The apparatus according to claim 1, wherein light of the second input light beam passes through the sample chamber substantially perpendicular to the direction of the first input light beam.

10. The apparatus according to claim 2,
wherein the second optical elements comprise reflection elements for changing the direction of the second input light beam.

11. The apparatus according to claim 1,
wherein the second input light beam partially propagates via a reference path comprising no sample, yielding a third output light beam.

12. The apparatus according to claim 1,
wherein the second input light beam can be switched between different spectra.

13. The apparatus according to claim 1,
wherein a magnetic field generator is provided for generating a magnetic field inside the sample chamber.

14. The apparatus according to claim 1,
wherein the sample chamber is elongated with an axial extension perpendicular to a direction of the first input light beam.

15. The method of claim 3, further comprising acts of:
partially propagating the second input light beam via a reference path comprising no sample, to yield a third output light beam; and
comparing the second and the third output light beams for distinguishing changes which originate from variations of the second input light beam from effects caused by the sample.

* * * * *